(12) United States Patent
Lang et al.

(10) Patent No.: US 7,654,263 B2
(45) Date of Patent: Feb. 2, 2010

(54) BREATHING MASK ARRANGEMENT AND A FOREHEAD SUPPORT DEVICE FOR SAME

(75) Inventors: Bernd Lang, Gräfelfing (DE); Achim Biener, Aulkirchon (DE); Dieter Heidmann, Geretsried (DE); Harald Vogele, Gauting (DE); Stefan Madaus, Krailling (DE)

(73) Assignee: Map Medizin-Technologie GmbH, Martinsried (DE)

( * ) Notice: Subject to any disclaimer, the term of this patent is extended or adjusted under 35 U.S.C. 154(b) by 433 days.

(21) Appl. No.: 11/128,399

(22) Filed: May 13, 2005

(65) Prior Publication Data

US 2005/0211252 A1 Sep. 29, 2005

Related U.S. Application Data

(63) Continuation of application No. 10/221,572, filed as application No. PCT/EP02/02877 on Mar. 14, 2002, now Pat. No. 7,000,614.

(30) Foreign Application Priority Data

Jan. 17, 2002 (DE) ................................ 102 01 682

(51) Int. Cl.
*A62B 18/08* (2006.01)
(52) U.S. Cl. ............................. 128/207.11; 128/207.13; 128/206.24
(58) Field of Classification Search ............ 128/205.25, 128/206.11, 206.12, 206.13, 206.16, 206.18, 128/206.21, 206.23, 206.24, 206.25, 206.26, 128/206.27, 206.28, 207.11, 207.13
See application file for complete search history.

(56) References Cited

U.S. PATENT DOCUMENTS

| 781,516 A | 1/1905 | Guthrie |
| 812,706 A | 2/1906 | Warbasse |
| 1,081,745 A | 12/1913 | Johnston et al. |

(Continued)

FOREIGN PATENT DOCUMENTS

AU 91/77110 B 11/1991

(Continued)

OTHER PUBLICATIONS

European Search Report issued in Appln. No. EP 02714190.2 (Jul. 11, 2006).

(Continued)

*Primary Examiner*—Steven O Douglas
(74) *Attorney, Agent, or Firm*—Nixon & Vanderhye P.C.

(57) ABSTRACT

A breathing mask arrangement for feeding a respiratory gas to a patient includes a forehead support device, an arch body, a sealing lip means for bearing against the surface of the patient's face, a respiratory gas conduit means for feeding respiratory gas to a mask internal space defined by the arch body and in communication with the nose and/or mouth opening of the patient. The breathing mask arrangement includes an application structure for application of the sealing lip means jointly with the arch body, wherein the application structure has a carrier portion on which a respiratory gas conduit member in the form of a docking port is releasably mounted. The forehead support device includes a contact element provided in the application position of the breathing mask for bearing against the forehead region of the patient, and a holding device for holding the contact element in tiltably movable manner.

19 Claims, 10 Drawing Sheets

U.S. PATENT DOCUMENTS

Figure 1:
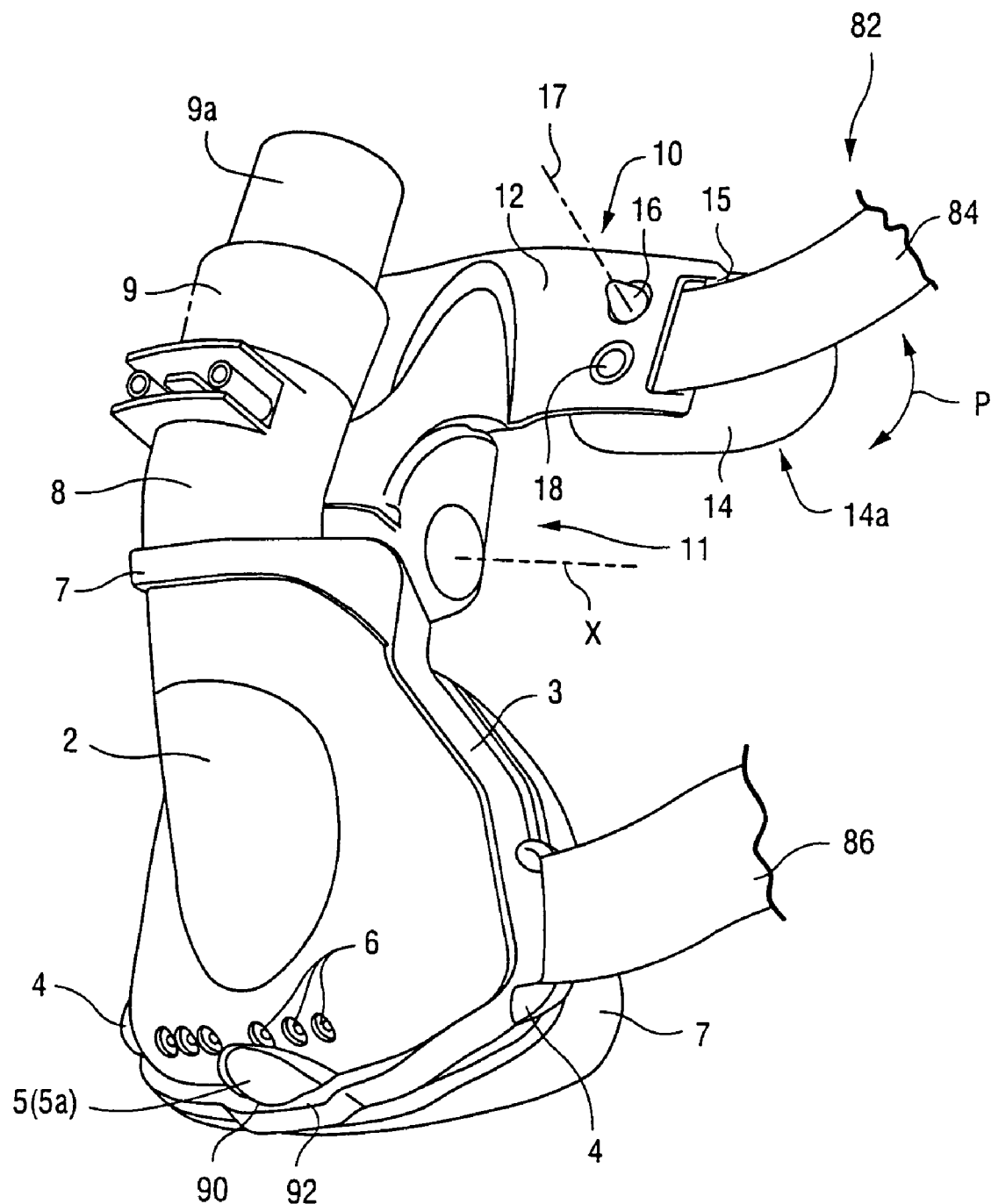

| | | |
|---|---|---|
| 1,192,186 A | 7/1916 | Greene |
| 1,653,572 A | 12/1927 | Jackson |
| 1,926,027 A | 9/1933 | Biggs |
| 2,123,353 A | 7/1938 | Catt |
| 2,245,658 A | 6/1941 | Erickson |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |
| 2,438,058 A | 3/1948 | Kincheloe |
| 2,578,621 A | 12/1951 | Yant |
| 2,590,006 A | 3/1952 | Gordon |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,750,333 A | 8/1973 | Vance |
| 3,752,157 A | 8/1973 | Malmin |
| 3,779,164 A | 12/1973 | Rollins |
| 3,796,216 A | 3/1974 | Schwarz |
| D231,803 S | 6/1974 | Huddy |
| 3,830,230 A | 8/1974 | Chester |
| 4,077,404 A | 3/1978 | Elam |
| D250,131 S | 10/1978 | Lewis et al. |
| 4,120,302 A | 10/1978 | Ziegler |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,558,710 A | 12/1985 | Eichler |
| D285,496 S | 9/1986 | Berman |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| H397 H | 1/1988 | Stark |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,807,617 A * | 2/1989 | Nesti ..................... 128/205.12 |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Snook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,027,809 A | 7/1991 | Robinson |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,069,205 A | 12/1991 | Urso |
| D323,908 S | 2/1992 | Hollister et al. |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,245,995 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,322,059 A | 6/1994 | Walther |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |

| | | | | | |
|---|---|---|---|---|---|
| 5,570,689 | A | 11/1996 | Starr et al. | DE | 284 800 C | 11/1913 |
| D377,089 | S | 12/1996 | Starr et al. | DE | 459 104 | 4/1928 |
| 5,592,938 | A | 1/1997 | Scarberry et al. | DE | 701 690 | 1/1941 |
| 5,608,647 | A | 3/1997 | Rubsamen et al. | DE | 159396 | 6/1981 |
| 5,642,730 | A | 7/1997 | Baran | DE | 3015279 A1 | 10/1981 |
| 5,647,355 | A | 7/1997 | Starr et al. | DE | 3345067 A1 | 6/1984 |
| 5,647,357 | A | 7/1997 | Barnett et al. | DE | 3537507 | 4/1987 |
| 5,649,532 | A | 7/1997 | Griffiths | DE | 3539073 A1 | 5/1987 |
| 5,649,533 | A | 7/1997 | Oren | DE | 4004157 C1 | 4/1991 |
| 5,655,520 | A | 8/1997 | Howe et al. | DE | 4343205 A1 | 6/1995 |
| 5,655,527 | A | 8/1997 | Scarberry et al. | DE | 29715718 | 10/1997 |
| 5,657,493 | A | 8/1997 | Ferrero et al. | DE | 197 35 359 | 1/1998 |
| 5,657,752 | A | 8/1997 | Landis et al. | DE | 297 23 101 U1 | 7/1998 |
| 5,662,101 | A | 9/1997 | Ogden et al. | DE | 298 10846 U1 | 8/1998 |
| 5,666,946 | A | 9/1997 | Langenback | DE | 198 17 332 A1 | 1/1999 |
| 5,685,296 | A | 11/1997 | Zdrojkowski et al. | DE | 198 08 105 A1 | 9/1999 |
| 5,687,715 | A | 11/1997 | Landis et al. | DE | 20005346 | 5/2000 |
| 5,715,814 | A | 2/1998 | Ebers | DE | 29923141 U | 5/2000 |
| 5,724,965 | A | 3/1998 | Handke et al. | DE | 200 17 940 | 12/2000 |
| 5,746,201 | A | 5/1998 | Kidd | DE | 200 17 940 | 2/2001 |
| 5,813,423 | A | 9/1998 | Kirchgeorg | DE | 199 54 517 A1 | 6/2001 |
| 5,832,918 | A | 11/1998 | Pantino | DE | 10045183 | 5/2002 |
| D402,755 | S | 12/1998 | Kwok | EP | 0 054 154 | 10/1981 |
| 5,921,239 | A | 7/1999 | McCall et al. | EP | 0 252 052 A1 | 1/1988 |
| 5,937,851 | A | 8/1999 | Serowski et al. | EP | 0 264 772 A1 | 4/1988 |
| D423,096 | S | 4/2000 | Kwok | EP | 0 386 605 A1 | 2/1990 |
| 6,044,844 | A | 4/2000 | Kwok et al. | EP | 0427474 A2 | 5/1991 |
| D428,987 | S | 8/2000 | Kwok | EP | 0 462 701 A1 | 12/1991 |
| 6,098,205 | A | 8/2000 | Schwartz et al. | EP | 0 602 424 | 11/1993 |
| 6,112,746 | A | 9/2000 | Kwok et al. | EP | 0 608 684 A1 | 8/1994 |
| 6,119,693 | A | 9/2000 | Kwok et al. | EP | 0 0697 225 | 7/1995 |
| 6,123,071 | A | 9/2000 | Berthon-Jones et al. | EP | 178 925 A2 | 4/1996 |
| 6,152,137 | A | 11/2000 | Schwartz et al. | EP | 0 747 078 A2 | 12/1996 |
| D439,326 | S | 3/2001 | Hecker et al. | EP | 0 821 978 | 2/1998 |
| D443,355 | S | 6/2001 | Gunaratnam et al. | EP | 1099452 | 5/2001 |
| 6,257,237 | B1 | 7/2001 | Suzuki | EP | 1205205 | 11/2001 |
| 6,341,606 | B1 | 1/2002 | Bordewick et al. | FR | 2 574 657 A1 | 6/1986 |
| 6,374,826 | B1 | 4/2002 | Gunaratnam et al. | FR | 2 658 725 A1 | 8/1991 |
| 6,397,847 | B1 | 6/2002 | Scarberry et al. | FR | 2 749 176 | 12/1997 |
| 6,463,931 | B1 | 10/2002 | Kwok et al. | GB | 1395391 | 5/1975 |
| D468,823 | S | 1/2003 | Smart | GB | 1 467 828 | 3/1977 |
| 6,520,182 | B1 | 2/2003 | Gunaratnam | GB | 2145335 A | 3/1985 |
| 6,532,961 | B1 | 3/2003 | Gunaratnam et al. | GB | 2147506 A | 5/1985 |
| 6,557,556 | B2 | 5/2003 | Kwok | GB | 2 186 801 | 8/1987 |
| 6,595,214 | B1 | 7/2003 | Hecker | GB | 2 267 648 A | 12/1993 |
| 6,631,718 | B1* | 10/2003 | Lovell .................. 128/206.24 | GB | 2 164 569 A | 3/1996 |
| D484,237 | S | 12/2003 | Lang et al. | JP | 09/216240 A | 8/1997 |
| 6,679,261 | B2 | 1/2004 | Lithgow et al. | JP | 11-000397 | 1/1999 |
| 6,691,707 | B1 | 2/2004 | Gunaratnam et al. | JP | 2000-515784 | 11/2000 |
| 6,691,708 | B2 | 2/2004 | Kwok et al. | WO | WO 80/01044 | 5/1980 |
| D492,992 | S | 7/2004 | Guney et al. | WO | WO 82/03548 | 10/1982 |
| 6,789,543 | B2 | 9/2004 | Cannon | WO | WO 86/06969 | 12/1986 |
| 7,059,326 | B2 | 6/2006 | Heidmann et al. | WO | WO 87/01950 | 4/1987 |
| 2003/0019496 | A1 | 1/2003 | Kopacko et al. | WO | WO 91/03277 | 3/1991 |
| 2003/0034034 | A1 | 2/2003 | Kwok et al. | WO | WO 92/15353 | 9/1992 |
| 2003/0062048 | A1 | 4/2003 | Gradon | WO | WO 92/20395 | 11/1992 |
| 2003/0089373 | A1 | 5/2003 | Gradon | WO | WO 93/01854 | 2/1993 |
| 2003/0221691 | A1 | 12/2003 | Biener et al. | WO | WO 94/02190 | 2/1994 |
| 2004/0045550 | A1 | 3/2004 | Lang et al. | WO | WO 94/16759 | 8/1994 |
| 2004/0045551 | A1 | 3/2004 | Eaton | WO | WO 94/20051 | 9/1994 |
| 2004/0177850 | A1 | 9/2004 | Gradon | WO | WO 95/02428 | 1/1995 |
| 2004/0255949 | A1 | 12/2004 | Heidmann et al. | WO | WO 96/17643 | 6/1996 |
| 2006/0191538 | A1 | 8/2006 | Lang et al. | WO | WO 96/25983 | 8/1996 |
| | | | | WO | WO 96/39206 | 12/1996 |
| | | FOREIGN PATENT DOCUMENTS | | WO | WO 97/07847 | 3/1997 |
| | | | | WO | WO 97/41911 | 11/1997 |
| AU | | 94/64816 B | 12/1994 | WO | WO 98/04310 | 2/1998 |
| AU | | 95/16178 B | 7/1995 | WO | WO 98/11930 | 3/1998 |
| AU | | 32914/95 | 2/1996 | WO | WO 9812965 | 4/1998 |
| AU | | 9459430 | 2/1996 | WO | WO 98/18514 | 5/1998 |
| AU | | A 41018/97 | 4/1998 | WO | WO 98/24499 | 6/1998 |
| AU | | A 89312/98 | 1/1999 | WO | WO 98/26829 | 6/1998 |
| CA | | 1039144 | 9/1928 | WO | WO 98/26830 | 6/1998 |

| | | |
|---|---|---|
| WO | WO 9834665 | 8/1998 |
| WO | WO 98/48878 | 11/1998 |
| WO | WO 9943375 | 9/1999 |
| WO | WO 99/58181 | 11/1999 |
| WO | WO 99/65554 | 12/1999 |
| WO | WO 00/78384 | 2/2000 |
| WO | WO 00/21600 | 4/2000 |
| WO | WO 00/57942 | 10/2000 |
| WO | WO 00/69521 | 11/2000 |
| WO | WO 00/78384 | 12/2000 |
| WO | WO 0078381 | 12/2000 |
| WO | WO 01/97892 | 12/2001 |
| WO | WO 02/32491 | 4/2002 |
| WO | WO 03/059427 | 7/2003 |
| WO | WO 2004/022145 | 3/2004 |
| WO | WO 2004022144 | 3/2004 |
| WO | WO 2004022145 | 3/2004 |
| WO | WO/2004/078228 | 9/2004 |

OTHER PUBLICATIONS

Decision Dated Dec. 6, 2007 (Received on Feb. 4, 2008); Opposition hearing by Weinmann . . . against German Patent 101 51 984 (including English Translation of the Decision).
Various invoices relating to the "Somnomask," as well as a brochure of the model "Somnomask" of 1999.
Mask 1 Photographs, Respironics Inc., Reusable Full Mask (small) Part #452033 Lot #951108.
Mask 2 Photographs, Puritan—Bennett, Adam Curcuit, Shell Part #231700, Swivel Part #616329-00, Pillows (medium) Part #616324.
Mask 3 Photographs, DeVilbiss Healthcare Inc., Devilbiss Seal-Ring and CPAP Mask Kit (medium), Part #73510-669.
Mask 4 Photographs, Respironics Inc., Monarch Mini Mask with Pressure Port. Part #572004, Monarch Headgear, Part #572011.
Mask 5 Photographs, Healthdyne Technologies, Nasal CPAP Mask (medium narrow), Part #702510.
Mask 6 Photographs, Healthdyne Technologies, Soft Series Nasal CPAP Mask, Part #702020.
Mask 7 Photographs, DeVilbiss Healthcare Inc., Small Mask and Seal Rings, Part #73510-668.
Mask 8 Photographs, Respironics Inc., Reusable Contour Mask (medium), Part #302180.
Mask 9 Photographs, Healthdyne Technologies, Healthdyne Large Headgear.
Mask 10 Photographs, Respironics Inc., Soft Cap (medium), Part #302142.
Mask 11 Photographs, Weinmann: Hamburg, Nasalmaskensystem mit Schalldämpfer (medium), Part #WN 23105.
Mask 12 Photographs, Life Care.
Mask 13 Photographs, Healthdyne Technologies.
Mask 14 Photographs, King System.
Mask 15 Photographs, Respironics Inc., Pediatric Mask.
Mask 16 Photographs, Hans Rudolph Inc., Hans Rudolph Silicone Rubber Face Mask/8900.
Photograph of Weinmann Mask, acquired prior to 1998.
Somotron CPAP—Gerat WM 2300 Instruction Manual, Weinmann Hamburg, 11 pages, 1991.
9 photographs of Weinmann mask, WM 23122, 1991.
The ResMed Range of Mask Systems, product brochure, Nov. 1995, 4 pages.
Product Brochure for ResMed "Sullivan® Mirage™—The Mirage is Real. A Perfect Fit—First Time," © 1997 ResMed Limited, 4 pages.
Product Brochure for ResMed "Sullivan® Mirage™—The Mirage is Real. A Perfect Fit—First Time,"© 1998 ResMed Limited, 4 pages.
Office Action dated Oct. 7, 2008, filed in Japanese Appln. No. 2003-537718 (English translation); 11 pages.

* cited by examiner

BREATHING MASK ARRANGEMENT AND A FOREHEAD SUPPORT DEVICE FOR SAME

CROSS-REFERENCE TO RELATED APPLICATIONS

This application is a continuation of U.S. application Ser. No. 10/221,572, filed Jan. 28, 2003, now U.S. Pat. No. 7,000, 614, which is the National Phase of International Application PCT/EP02/02877, filed Mar. 14, 2002, which designated the U.S. and that International Application was not published under PCT Article 21(2) in English, and claims the benefit of German Application No. DE 10201682.8, filed Jan. 17, 2002, each of which is incorporated herein by reference in its entirety.

BACKGROUND OF THE INVENTION

1. Field of the Invention

The invention concerns a breathing mask arrangement as can be used for example in the context of CPAP-therapy for treating sleep-related respiratory disturbances. The invention further concerns a forehead support device for a breathing mask arrangement.

2. Description of Related Art

In the context of what is referred to as CPAP-therapy a patient can be supplied by way of a breathing mask arrangement with a breathable gas, in particular ambient air at a pressure level which is above the ambient pressure level. The respiratory gas which is under pressure makes it possible to provide for pneumatic splinting of the upper respiratory tracts and thus to obviate any obstructions. In the course of implementing pressure respiration or CPAP-therapy the breathing mask arrangements which are required to supply the respiratory gas are usually worn by the patient over the entire sleep or rest phase of the patient. The breathing mask arrangement is usually supported by way of a sealing lip zone in the region around the nose of the person using the mask and by way of a forehead support device in the forehead region of the mask user. The holding forces required to apply the breathing mask arrangement can be afforded by a fixing device which for example has a headband which is passed around the back of the head of the mask user. Under some circumstances, in the region in which the sealing lip device is applied and in the contact region of the forehead support device, surface pressures can occur, which result in the level of comfort involved in wearing the breathing mask arrangement being seriously adversely affected. In dependence on the individual architecture of the face of the person wearing the mask, considerable mask-pressing forces are in part required in order to achieve the desired sealing integrity. In that situation, in the region of the zones where the breathing mask bears against the face of the patient, unacceptably clearly visible pressure points may also be caused in the forehead region.

BRIEF SUMMARY OF THE INVENTION

The object of the invention is to provide a breathing mask arrangement which can be reliably fixed in a correct application position and which is additionally distinguished by a high level of wearing comfort. Attainment of the object in accordance with the invention In accordance with the invention that object is attained by a breathing mask arrangement comprising an arch body, a sealing lip means for bearing against the surface of the face of a mask user, a respiratory gas conduit means for feeding respiratory gas to a mask internal space which is defined by the arch body and which is in communication with the nose and/or mouth opening of the user of the mask, and an application structure for application of the sealing lip means jointly with the arch body, wherein the application structure has a carrier portion on which a respiratory gas conduit member is mounted.

In that way it is advantageously possible to provide a breathing mask arrangement which is of a robust structure and which can be cleaned in an advantageous manner and which is distinguished by a high level of sealing integrity.

In accordance with a particularly preferred embodiment of the invention the respiratory gas conduit member is in the form of a tube connection. Such a tube connection is preferably made from dishwasher-resistant plastic material so that the respiratory gas conduit member can be cleaned at comparatively high temperatures and in the process sterilised. The tube connection is preferably of such a configuration that its inside diameter is in the region of 12 to 34 mm. The tube connection can be of a substantially circular or preferably polygonal cross-section. The tube connection can be in the form of a conduit bend which provides for a slight change in direction of the flow of respiratory gas through an angle in the range of from 0 to 45°.

The conduit member which in particular is in the form of a tube connection is preferably releasably mountable to the carrier portion. A latching device is preferably provided for coupling the respiratory gas conduit member to the carrier portion. In accordance with a particular aspect of the present invention that latching device is advantageously in the form of a bayonet or rotational latching device.

The application structure of the breathing mask arrangement advantageously includes a frame portion which can be releasably coupled to the sealing lip means and/or to the arch body. Preferably the frame portion is designed in such a way that it embraces the arch body in a ring or loop configuration. The carrier portion is advantageously made from a plastic material and is provided with holding members, by way of which the carrier portion can be coupled for example to a lower web band arrangement of a headband. Advantageously those holding members are in the form of holding loops or clips, through which an end portion of the above-mentioned lower web band arrangement can be passed. The holding loops are preferably formed integrally with the carrier portion. The internal peripheral wall of a through opening formed by the holding loops is preferably of a configuration which, in regard to the moulding tool, permits removal of the holding loops from the mould without involving the use of a sliding pusher member.

The carrier portion provided for fixing the respiration gas conduit member is advantageously formed integrally with the frame portion. In that respect the carrier portion is advantageously designed in such a way that it has an insert opening into which the respiratory gas conduit member can be releasably inserted. The carrier portion is preferably arranged in such a way that it extends substantially perpendicularly to a frame surface defined by the frame portion.

In the region of the insert opening, the carrier portion preferably forms those coupling structures which can be brought into engagement with the respiratory gas conduit member which is in the form of the tube connection.

The arch body preferably comprises a coupling portion, by way of which the arch body can be sealingly connected to the respiratory gas conduit member. Preferably the arch body is produced from an elastomer material and fitted with elastic expansion thereof on to a portion of the tube connection, which is passed through the insert opening and which penetrates to the sealing lip means. Preferably, a peripheral bead or ridge is provided on that portion of the tube connection, which extends as far as the sealing lip means, by means of which peripheral bead the arch body and the tube connection are reliably held in the joined condition.

In accordance with a particularly preferred embodiment of the invention the arch body is formed integrally with the sealing lip means. In that way it is advantageously possible to avoid gaps or joints in the transitional region between the sealing lip means and the arch body. In addition it is advantageously possible for the sealing lip means and the arch body to be inserted in the form of an integral elastomer component into the frame portion.

In accordance with a particularly preferred embodiment, particularly reliable discharge of respiratory gas loaded with $CO_2$ to the ambient atmosphere is attained in that the arch body is provided with openings through which the respiratory gas which is under pressure in the internal region of the arch body can escape to the ambient atmosphere. The openings are preferably such that the cross-section thereof enlarges in the outlet direction. Those outlet openings are preferably arranged in such a way that they are disposed as closely as possible to the region which, in the position of application of the breathing mask arrangement, is adjacent to the nasal openings of a user of the mask.

In accordance with a particular aspect of the present invention the application structure includes a forehead supporting device for supporting the breathing mask arrangement in the forehead region of the user of the mask. The forehead supporting device is advantageously connected by way of a pivot device to the frame portion which embraces the arch body. By virtue of that configuration it is advantageously possible for the position of the forehead supporting device to be adapted to the individual architecture or configuration of the face of the user of the mask. Preferably the pivot device includes an arcuate track guide means by which the forehead supporting device can be variably positioned.

The respiratory gas conduit member which is preferably releasably couplable to the carrier portion advantageously forms a docking port which for example can also form part of a rotary coupling structure. It is possible to provide on the docking port further connecting devices, in particular small tube connections, by way of which for example a pressure measuring hose can be coupled to the breathing mask arrangement or possibly an additional supply of oxygen can be effected.

The forehead supporting device is preferably made from a thermoplastic material and provided with a forehead cushion means. The forehead cushion means is preferably formed by elastomer elements which are of a pad-like configuration and which can be coupled by way of a plug connecting structure to the receiving portion of the forehead supporting device, said receiving portion preferably being of a loop-like configuration. In that case the forehead supporting device is preferably designed in such a way that the elastomer elements can be fitted to the forehead supporting device at different locations. Preferably the elastomer elements are also of such a configuration that, by virtue of the way in which they are fixed to the loop portion, it is also to achieve different positions of the contact regions of the elastomer elements on the forehead of the user of the mask. The elastomer elements are preferably made from a silicone rubber material and in the region of their contact surface are so shaped that transmission of the contact forces to the surface of the forehead of the user of the mask takes place under a physiologically well compatible surface pressure. That can be achieved in particular by the elastomer elements being provided, on a rear side remote from their contact side, with an eccentrically arranged support foot which permits a tilting movement of the contact portion which bears against the user of the mask.

Preferably, also provided on the loop portion are coupling portions which permit coupling of the forehead supporting device to an upper forehead band arrangement of a headband. Those coupling portions can be in the form of a band strip. It is also possible for the forehead supporting device to be fixed for example by way of a hook-and-loop fastener to a preferably cushioned forehead band arrangement.

In accordance with a further aspect of the invention, another object of the invention is to prevent the occurrence of any pressure points in the forehead region in connection with the use of breathing masks.

In accordance with the invention that object is attained by a forehead support device for a breathing mask comprising a contact element which is provided in the application position for bearing against the forehead region of a user of the mask, wherein there is provided a holding device for holding the contact element movably.

By virtue thereof it is advantageously possible to ensure that a breathing mask arrangement is supported in the forehead region of a patient under a markedly reduced surface pressure against the tissue of the patient. The mobility of the contact element, which is provided in accordance with the invention, means that it can automatically adapt to the individual curvature of the forehead region of the user of the mask. In that way it is further advantageously possible for the contact element to afford a large surface area, whereby it is advantageously possible to achieve a marked reduction in the surface pressure.

An embodiment of the forehead support device, which is preferred in accordance with a particular aspect of the present invention, is afforded in that the holder is in the form of a pivotal holder. That pivotal holder advantageously permits a tilting movement of the contact element about at least one axis substantially parallel to the usual contact orientation. That pivotal holder can preferably be formed by a pivot or hinge device which in accordance with a particularly preferred embodiment includes a ball joint. As an alternative thereto or also in combination with that configuration, it is possible for the pivot device to be formed by an elastomer structure. The range of movement of the holder of the contact element is preferably in the range of 10-30°. It is possible to take sufficient account of all possible forehead architectures within that angular range.

In accordance with a particular aspect of the present invention the contact element is formed from an elastomer material, for example a fully transparent or coloured silicone rubber material. Particularly in this embodiment the contact element is preferably of a pad-like or plate-like configuration. In that case, the contact element is preferably concavely inwardly curved in such a way that a defined distribution in terms of surface pressure is afforded when the contact element is applied to the surface of the forehead. In accordance with a particularly preferred embodiment of the invention that surface pressure is so selected that, within a predetermined spacing from the edge of the contact element, there is a substantially uniform surface pressure, with the surface pressure gradually decreasing outwardly in the edge region of the contact element.

In accordance with a particularly preferred embodiment of the invention the forehead support device includes a plurality of and preferably two mutually adjacently arranged contact elements. The contact elements are preferably arranged in such a way that in the application position of a breathing mask arrangement, they are positioned above the left and right eyebrows of the user of the mask. The two contact elements are preferably connected together by way of a flexible bridge or strap device. In that way, it is possible on the one hand to achieve a greater increase in the contact area while at the same time the possibility of the contact elements twisting relative to each other can be limited in a defined manner. Particularly in this embodiment the two contact elements are preferably formed integrally with each other. The configuration of the contact elements in a plan view is not limited to substantially circular external contours. For example it is also possible to adopt elliptical or other polygonal external contours.

The pivot device for pivotably movably mounting the respective contact element is preferably also formed integrally with the contact element. A defined pivot character can be achieved by virtue of suitable geometrical configuration of the pivot device.

The pivot device is preferably arranged in such a way that it is disposed on or at least near the line of action of a force which extends through a centre point in terms of surface pressure of the respective contact element. That still further promotes rendering the distribution of surface pressure uniform.

The contact elements are preferably profiled in such a way that the contact element is prevented from being applied by suction to the surface of the forehead of the patient. Suction of the forehead support device on the surface of the forehead of the patient can further also be obviated by the contact element being provided with through bores or also with passages, through which air can pass into an intermediate region between the contact element and the forehead of the user of the mask.

The ball joint structures advantageously provide for good adaptability to the horizontal and vertical configuration of the forehead of the user of the mask. The pivot device—in particular the ball joint means—can also be designed to be lockable. The pivot device can also preferably be tiltable in a particularly advantageous manner about given axes—in particular about a horizontal axis. The curvature of the contact element can be so selected that different radii of curvature are afforded in the horizontal and vertical directions. The radii of curvature are preferably smaller than the usual radii of curvature of a forehead.

As an alternative to ball joint structures it is also possible to adopt cardanic suspension means, for example by means of a pivot pin. The angle of pivotal movement of the pivot device is preferably limited to a predetermined abutment angle. The material properties of the contact element are preferably so selected that it has a substantially anti-bacterial action and possibly acts to promote the healing of wounds.

Advantageously, a cushion means, in particular a gel body cushion means, or also an air or liquid cushion means, can be provided in the region of the contact surface. In that case, by varying the amount of liquid, air or gel used, it is advantageously possible to adjust the position of the breathing mask relative to the user.

Advantageously the mounting position of the contact element is adjustably variable. As an alternative thereto—or also in combination with this feature—it is also possible to provide a plurality of coupling options so that it is possible to achieve varying spacings on the forehead, by suitable selective coupling. It is possible to implement coarse adjustment by for example two, preferably three or also more coupling options, and to implement preferably stepless fine adjustment within a limited fine adjustment range. It is possible to permit a plurality of permutation options, in which case the individual coupling permutations result in respectively different settings in terms of the spacing relative to the forehead. It is also possible to provide clamping structures, by means of which stepless adjustment of the spacing relative to the forehead is possible. The coupling means can be so designed that a defined adhesive location is achieved, so that a setting which is individually steplessly adapted is durably maintained by adhesive means.

In accordance with a particularly preferred embodiment of the invention a particularly high level of wearing comfort is achieved in that the surface portions of the contact element, which come into contact with the surface of the skin of the user of the mask, have a surface which is velvety matte. In accordance with a particularly preferred embodiment of the invention, at least in the region of the contact surface of the contact element, there is provided a surface structure for affording a self-cleaning effect. Such a surface structure may have for example lotus leaf surface structures. The contact element may also be provided with a gel body, at least in the region of the contact surface.

BRIEF DESCRIPTION OF THE SEVERAL VIEWS OF THE DRAWING(S)

Figure 2:
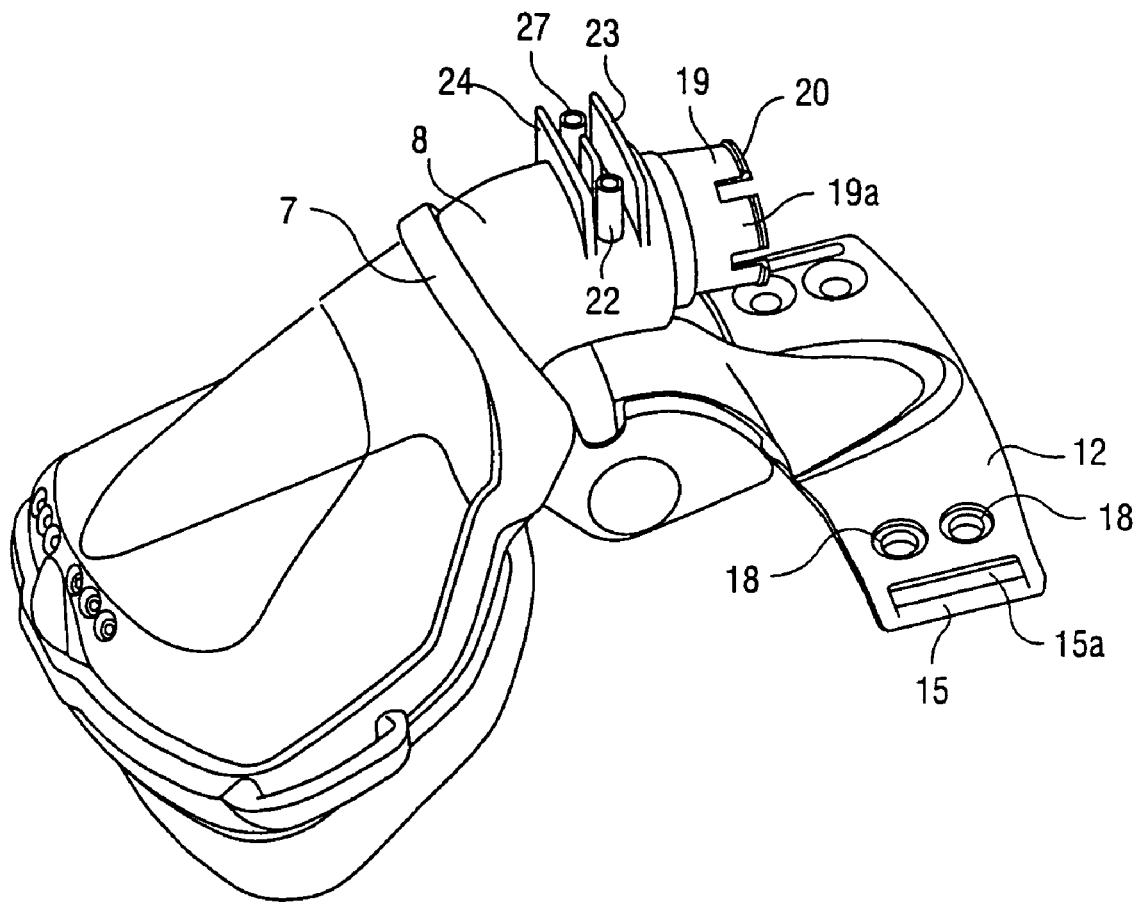
Figure 3:
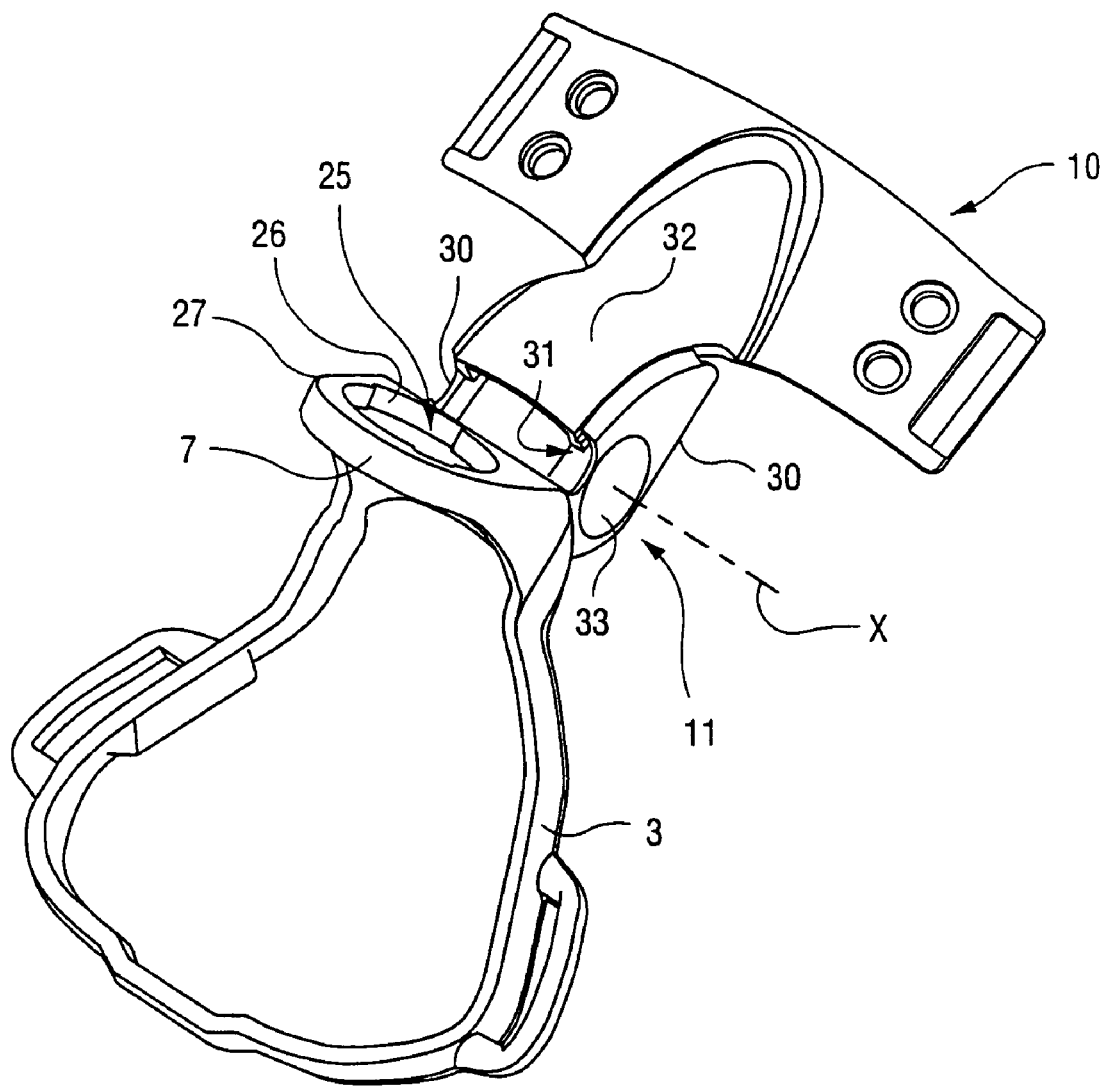
Figure 4:
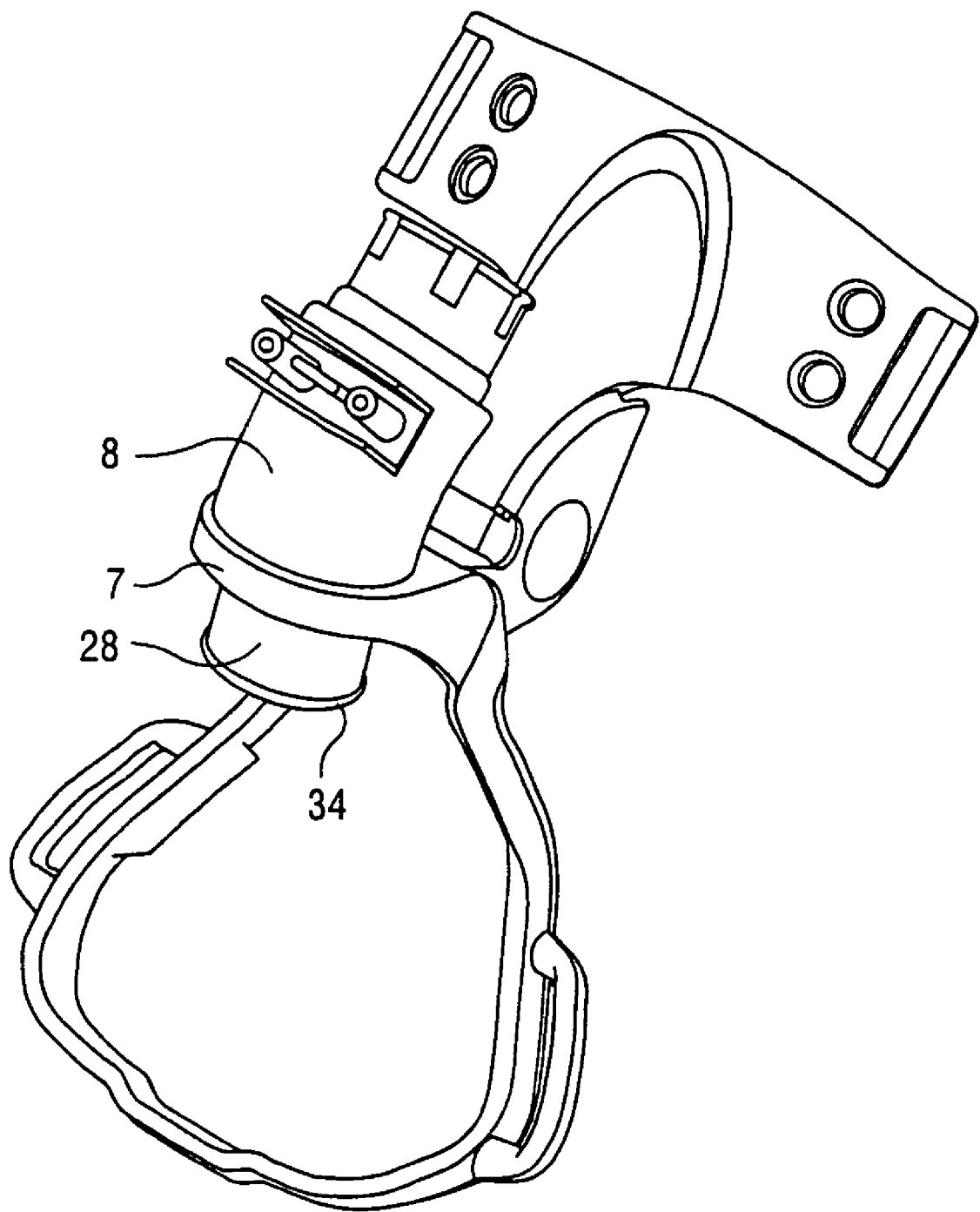
Figure 5:
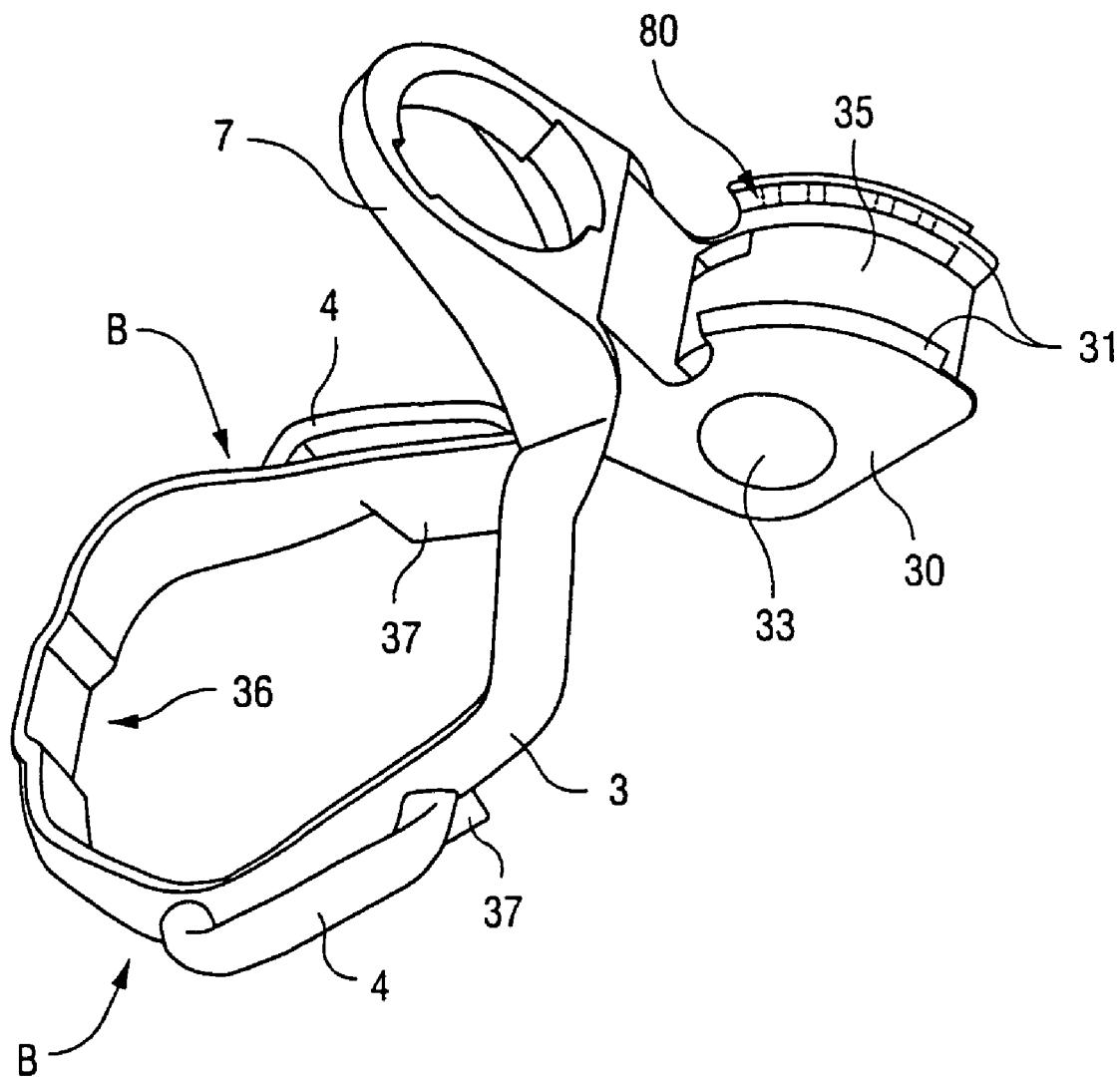
Figure 6:
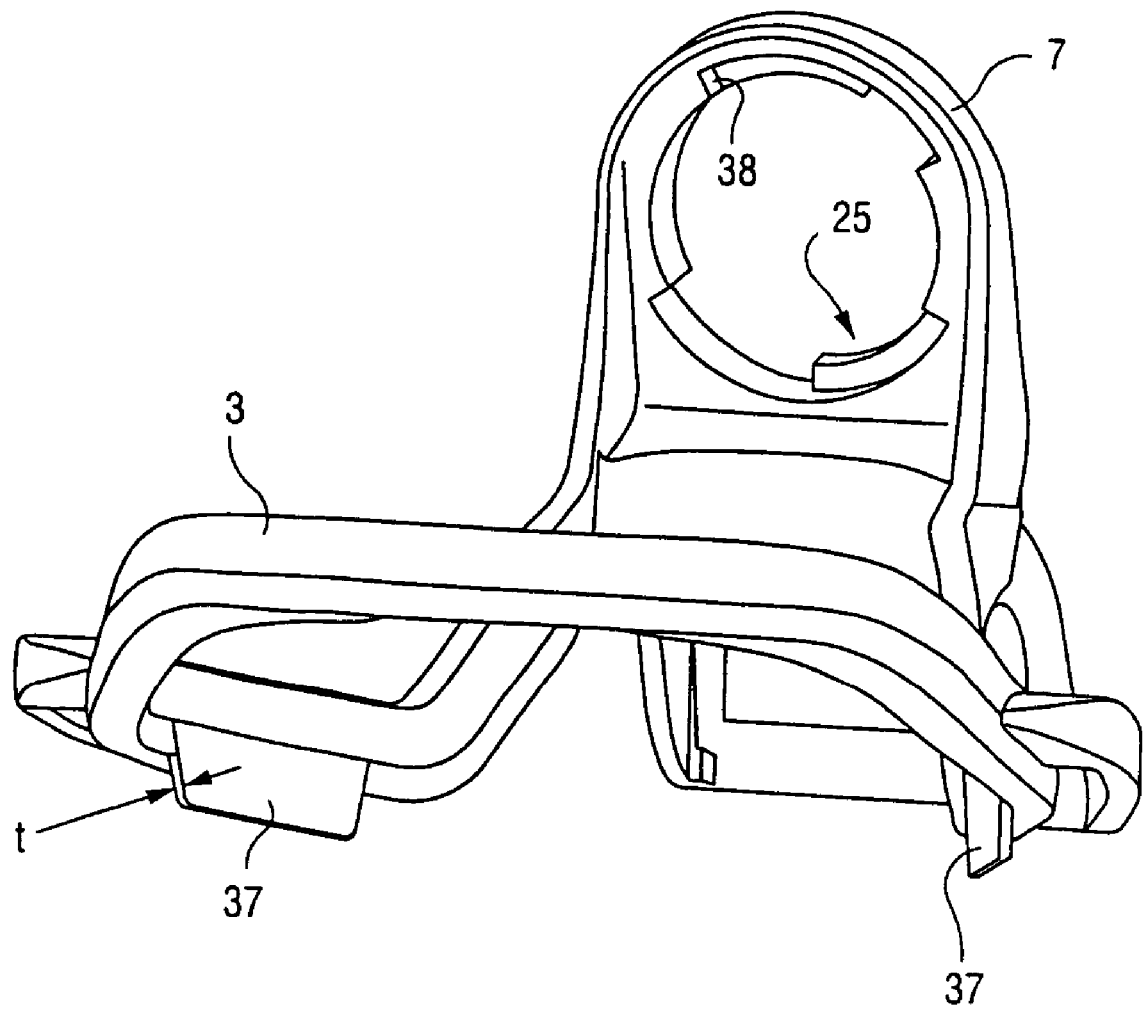
Figure 7:
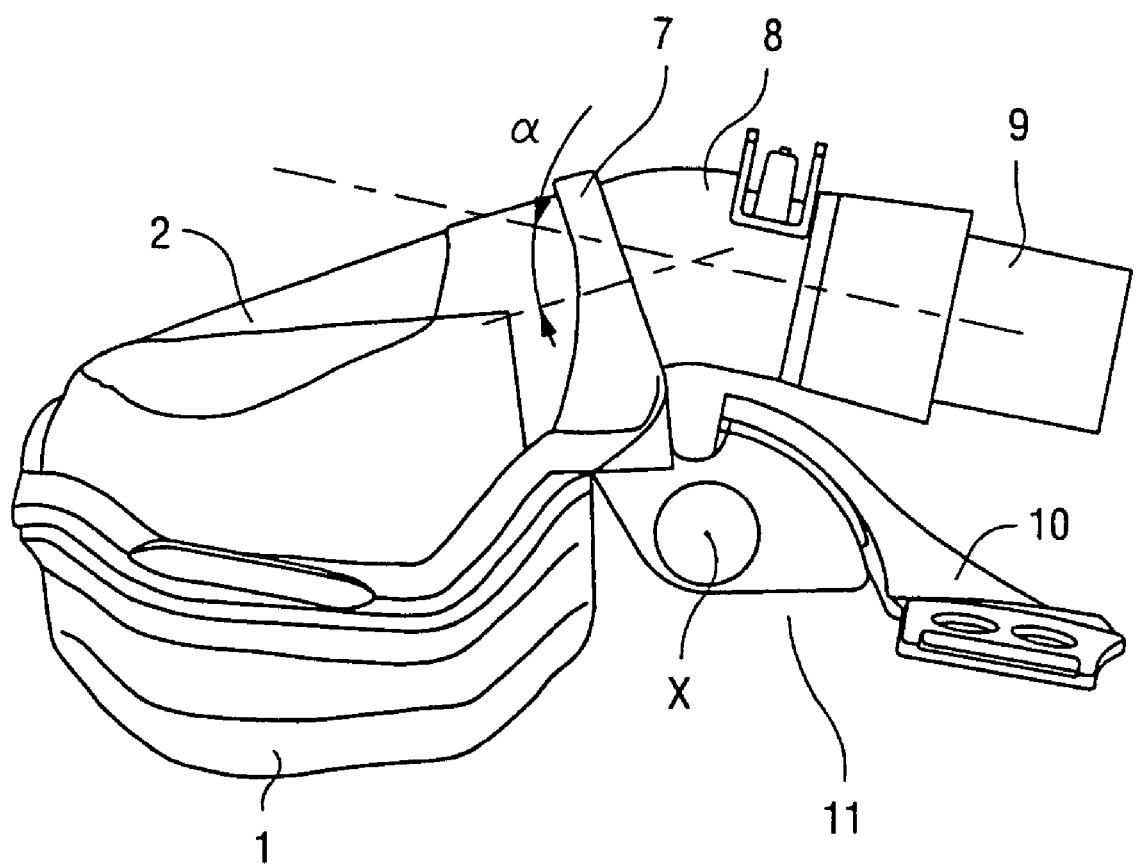
Figure 8:
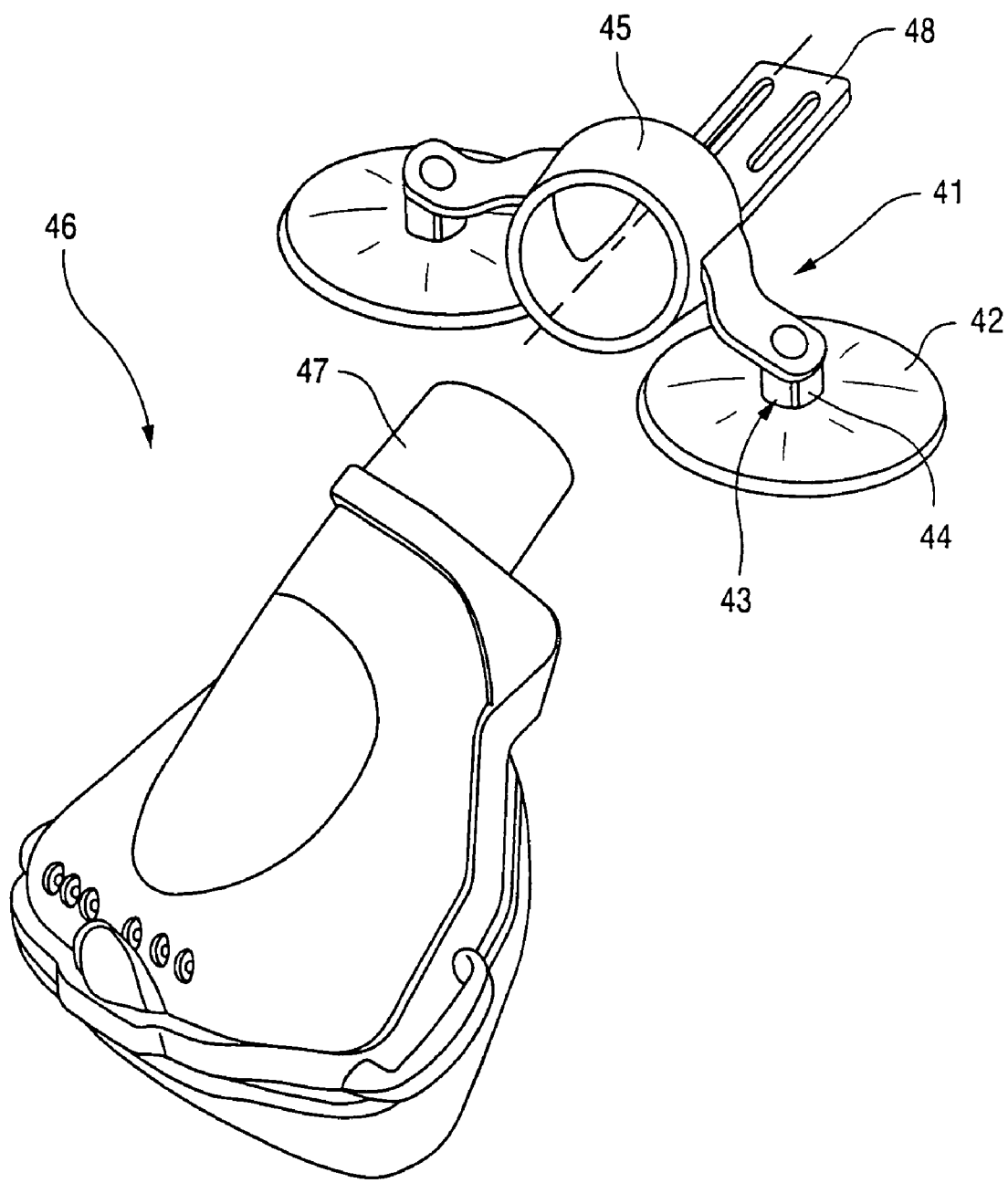
Figure 9:
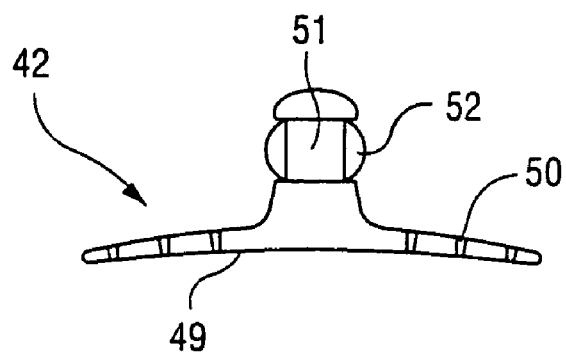
Figure 10:
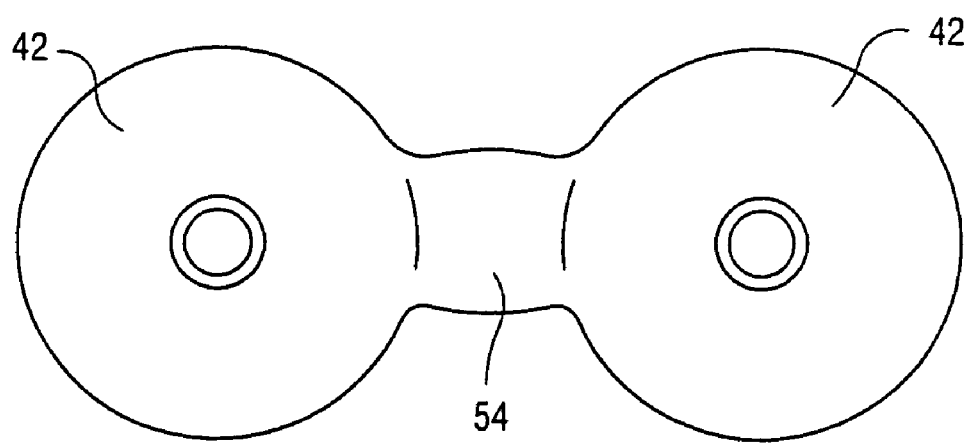
Figure 11:
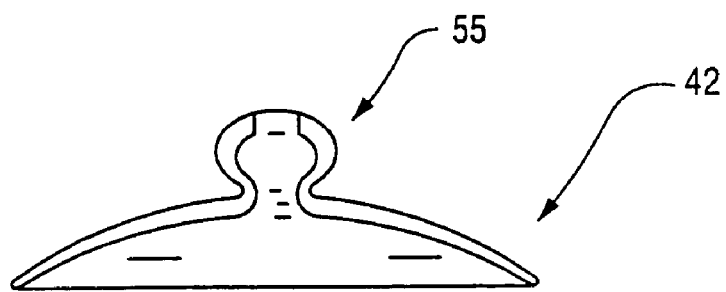
Figure 12:
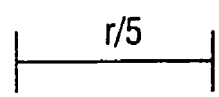
Figure 12:
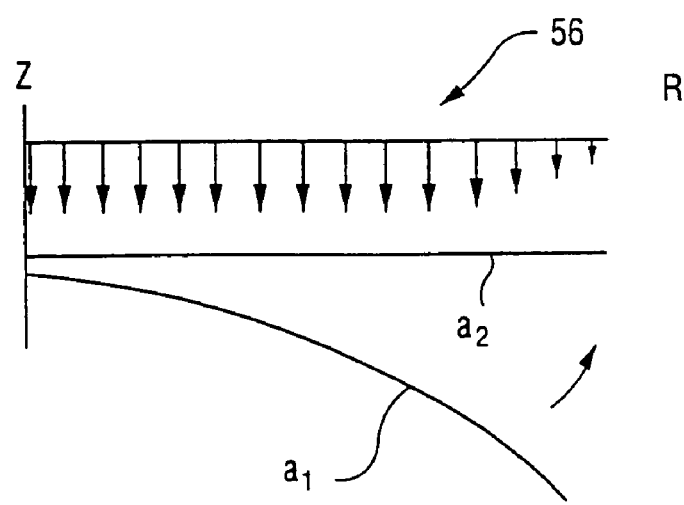

Further details and features of the invention will be apparent from the description hereinafter with reference to the drawings in which:

FIG. 1 shows a perspective view of a breathing mask arrangement according to the invention, FIG. 2 shows a further perspective view of the breathing mask arrangement according to the invention without hose connecting sleeve, FIG. 3 shows a perspective view of the application structure of the previously illustrated breathing mask arrangement, FIG. 4 shows a perspective view of the application structure with a docking port connected thereto, FIG. 5 shows a perspective view of an integral member formed from a carrier portion and a frame portion, FIG. 6 shows a further perspective view of the integral member shown in FIG. 5 to describe the latching device provided for coupling the docking port, FIG. 7 shows a side view of the breathing mask arrangement according to the invention, FIG. 8 shows a simplified perspective view of a forehead support device with two pivotably mounted pad-like contact elements and by way of indication a breathing mask, FIG. 9 shows a simplified sectional view to illustrate a preferred embodiment of a pivotably mounted contact element, FIG. 10 shows a plan view of two contact elements which are formed integrally with each other, each of which is individually provided with a pivotal mounting means, FIG. 11 shows a further embodiment of a contact element with a concavely curved contact surface and a part-spherical portion for pivotably mounting the contact element, and FIG. 12 shows a sketch to describe a preferred distribution of surface pressure from a central region of the contact element in its variation from a centre region of the contact element towards the edge region thereof.

DETAILED DESCRIPTION OF PREFERRED EMBODIMENTS

The breathing mask arrangement shown in FIG. 1 includes a sealing lip means 1 made from an elastomer material, in particular silicone rubber, and an arch body 2. The sealing lip means 1 is designed in such a way that it lines a receiving opening provided to receive the nose region of a user of the mask, and in that situation preferably passes across the bridge of the nose and the upper lip region of the user of the mask. In this case the sealing lip means 1 is of a substantially saddle-shaped silhouette. In this embodiment, the sealing lip means 1 and the arch body 2 are made in one piece from an elastomer material and are accommodated in a frame portion 3.

The frame portion 3 is made from a plastic material and has holding clips or loops 4 which are produced integrally therewith. In the application position of the breathing mask arrangement the holding loops 4 are disposed at cheek level or at the level of the sides of the nose of the user of the mask and permit coupling of a lower web band arrangement 86 of a headband 82. For reliably coupling the arch body 2 to the frame portion 3, there is a retaining structure 5, by way of which the arch body 2 can be fixed to the frame portion 3 in the joining position by latching engagement therein. The retaining structure 5 includes a retaining nose 5a providing a first interlocking surface 90 which engages over a top side of the frame portion 3 providing a second interlocking surface 92.

Provided on the arch body 2 are a plurality of outlet openings 6 for the discharge of used respiratory gas to the ambient atmosphere.

The breathing mask arrangement further includes a carrier portion 7 which in this embodiment is formed integrally with the frame portion 3.

A respiratory gas conduit member which here is in the form of a docking port 8 is releasably fixed to the carrier portion 7. The docking port 8 includes an annular flange (not visible here) on to which a hose connecting sleeve 9 is rotatably movably fitted. The hose connecting sleeve 9 includes a hose connecting portion 9a on to which an end portion of a respiratory gas hose can be fitted.

The breathing mask arrangement according to the invention further includes a forehead supporting device 10 which is coupled movably to the frame portion 3 by way of an adjusting device 11.

The adjusting device 11 is of such a configuration that it permits a pivotal movement of the forehead supporting device 10 with respect to the frame portion 3 about the pivot axis X which is shown here. The adjusting device 11 includes a fixing mechanism, by which the forehead supporting device 10 and the frame portion 3 can be fixed in the selected relative position.

The forehead supporting device 10 includes a loop portion 12 to which forehead cushion elements 14 can be mounted. Provided on the loop portion 12, similarly to the frame portion 3, are holding loops or clips 15, for coupling the loop portion 12 to an upper web band arrangement 84 of a headband 82 provided for fixing the breathing mask arrangement in place (see FIG. 1).

The forehead cushion elements 14 are made from an elastomer material and, on their underside 14a which in the application position faces towards the user of the mask, form a contact surface involving a predetermined distribution in terms of surface pressure. The forehead cushion elements 14 are each coupled to the loop portion 12 by way of a respective push-in foot 16. The push-in foot 16 is provided eccentrically on the respective forehead cushion element 14 in such a way that pivoting the forehead cushion elements 14 about the axis 17 of the push-in foot, as indicated by the arrow P, makes it possible to achieve different contact positions for the underside 14a of the forehead cushion elements 14 on the surface of the forehead of the user of the mask. Different contact positions can be achieved by virtue of selection of the pivotal position of the forehead cushion element 14 and by virtue of selection of the receiving opening 18 provided to receive the push-in foot 16. In the embodiment illustrated here, two mutually spaced receiving openings 18 are provided in the loop portion 12, for each of the left and the right forehead cushion elements 14.

The forehead cushion elements 14 can be removed from the loop portion 12 by pulling the push-in feet 16 out of the receiving openings 18, as is shown in FIG. 2. In this embodiment, the centre lines of the receiving openings 18 are spaced from each other by approximately 10 mm. The eccentricity of the push-in foot 16 on the respective forehead cushion element 14 (see in that respect FIG. 1) is also about 10 mm. As a result of the eccentric arrangement of the push-in foot 16 and the spaced arrangement of the receiving opening 18, heightwise variability of the forehead cushion elements in a range of about 30 mm is achieved substantially perpendicularly to a line joining the eyebrows of the user of the mask. A variation in the contact position over a range of 20 mm is also possible in a lateral direction, that is to say in the direction of the above-mentioned line which joins the eyebrows. The holding loop 15 provided for coupling an upper web band arrangement is arranged in the proximity of the receiving openings 18 in such a way that the through opening 15a defined by the holding loop is covered over towards the user of the mask by the forehead cushion element 14.

In the view shown in FIG. 2 the hose connecting sleeve 9 shown in FIG. 1 has been removed from the docking port 8. It is possible in this view to see an annular flange 19 which is formed integrally with the docking port 8 and which has a plurality of tongue elements 19a which are elastically deflectable towards the centre of the through passage formed by the docking port 8. Provided on the tongue elements 19a is a retaining bead or ridge 20 which can be brought into engagement with an internal peripheral groove provided in complementary relationship on the hose connecting sleeve 9. The geometry of the retaining bead 20, the internal peripheral groove in the rotational sleeve 9 and the elasticity of the tongue elements 19a are so matched that the hose connecting sleeve 9 can be withdrawn from the annular flange 19 without involving the use of a tool, when a given pulling force is exceeded. The annular flange 19 and the hose connecting sleeve 9 are also designed to fit in such a way that the hose connecting sleeve 9 is easily rotatably carried on the annular flange 19.

In this embodiment the docking port 8 is provided with hose connecting portions 21, 22, on to which a plug or hose element can be fitted. The hose connecting portions 21, 22 each form a respective through passage which opens into the respiratory gas passage formed in the docking port 8. When not in use, the hose connecting portions 21, 22 can be closed by a plug or cap element (not shown) which is preferably fitted in frictionally locking relationship on the hose connecting portions 21, 22. In this embodiment the hose connecting portions 21, 22 are arranged recessed in a groove which is delimited by two upstanding groove walls 23, 24. The docking port 8 is coupled to the carrier portion 7 by way of a plug-in connecting structure.

The retaining connecting structure for coupling the docking port 8 to the carrier portion 7, as can be seen from the view in FIG. 3, in this embodiment, is in the form of a rotary latching or bayonet connecting structure 25. The bayonet connecting structure 25 includes two mutually diametrally opposite retaining bridges 27 which are separated from each other by insertion recesses 26. In the locking position the retaining bridges 27 come into engagement with two retaining projections which are provided on a push-in flange portion 28 (FIG. 4) of the docking port.

The carrier portion 7 is formed integrally with the frame portion 3 and in that respect forms the insert opening which is provided to receive the push-in flange portion 28 and which is partially lined by the retaining bridges 27. Provided in the transitional region between the carrier portion 7 and the frame portion 3 are two guide flanks 30 which are also provided integrally with the frame portion 3 and form part of the adjusting means 11. The guide flanks 30 form an arcuate guide means 31 in which a coupling portion 32 of the forehead supporting device 10 is displaceably guided. The arcuate guide means 31 and the region of the coupling portion 32, which is guided therein, are such that the forehead supporting device 10 and the frame portion 3 are movable relative to each other about the pivot axis X already shown in FIG. 1. Provided at the guide flanks 30 is an actuating zone 33, for applying the release force for moving the adjusting means 11 into a release position. The release force can be applied to the actuating zone in particular when gripping around the docking port 8 with the thumb and the index finger and applying the corresponding fingertips. As an alternative to the arcuate guide means 31 provided here, it is also possible for the adjusting means 11 to be of such a configuration that relative movement is made possible between the forehead supporting device 10 and the frame portion 3 along a path of movement which differs from an arcuate path. It is also possible to mount to the forehead supporting device 10 forehead cushion devices which in their structure differ from the forehead cushion elements 14 shown in FIG. 1.

FIG. 4 shows the application structure of the breathing mask arrangement according to the invention, in an assembly condition in which the docking port 8 according to the invention is inserted into the insert opening formed in the carrier portion 7 and correctly fixed in position by way of the bayonet closure device provided in the region of the insert opening. In this embodiment, the docking port 8 forms a conduit member which is in the nature of a pipe bend and by which the flow of respiratory gas flowing by way of the hose connecting sleeve 9 (FIG. 1) is diverted through an angle of about 30° towards the tip of the nose of the user of the mask. Feeding the respiratory gas in that way to the internal space in the mask, which is defined by the arch body 2 (FIG. 1), provides that the gas advantageously flows over the bridge of the nose of the user of the mask.

The modular structure of the breathing mask arrangement according to the invention makes it possible to implement a configuration of the breathing mask arrangement, which takes better account of the respective situation of use. The docking port 8 which is fitted into the carrier portion 7 has an insert connecting portion 28 which projects beyond the carrier portion 7 towards the frame portion 3. An insert opening portion of the arch body 2 can be fitted on to the insert connecting portion 28, with slight elastic expansion. Provided on the insert connecting portion 28 is a peripheral bead 34, by which the arch body 2 and the insert connecting portion 28 are held in a defined joint position. That peripheral bead 34 can come into engagement with an internal peripheral groove correspondingly provided in the arch body 2, or it can fit on an internal surface of the arch body 2. The carrier portion 7 and the docking port 8 are of such a configuration that the docking port 8 forms a respiratory gas conduit portion which bridges over the region of the bridge of the nose. That ensures that the field of vision is only slightly impaired.

FIG. 5 shows a further perspective view of the integral member forming the frame portion 3. The guide flanks 30 which are made in one piece with the frame portion 3 are of such a configuration that application of a release force to the actuating zones 33 urges the guide flanks 30 away from each other in the region of the arcuate guide means 31. In the present embodiment, for that purpose, a lever/tilting effect is produced by an arcuate leg 35. The return movement of the guide flanks 30 in the region of the arcuate guide means 31 takes place as a consequence of the elasticity of the material involved. The fixing effect can be achieved by virtue of frictionally locking clamping of the contact zones of the coupling portion 32, which are guided between the guide flanks 30. As an alternative thereto or in combination therewith, it is also possible to achieve the fixing effect by coupling in positively locking engagement, for example by the adoption of a fine tooth arrangement 80 (shown in dashed lines in FIG. 5).

Preferably, there is provided an abutment device which limits the maximum range of pivotal movement of the forehead supporting device 10 with respect to the frame portion 3. It is possible for that abutment device to be so designed that, for example by increasing the actuating forces applied to the actuating zone 33, the abutment device is moved into a condition in which the forehead supporting device 10 can be separated from the pivot structure connected to the frame portion 3.

The view illustrated in FIG. 5 also shows an outwardly recessed region 36 in the frame portion 3, which improves positioning and fixing of the arch body 2 in the frame portion 3. Positioning of the arch body 2 in the frame portion 3 is further promoted by two fixing plates 37 which are provided in the region of the holding loops 4 at the underside of frame portion 3 and which engage into clamping pocket portions provided in the transitional region of the sealing lip means 1 in the arch body 2. The frame portion 3 is of a substantially saddle-shaped silhouette and attains its maximum width in a region of the frame portion 3, which in the application position of the breathing mask arrangement is approximately at the height of the sides of the nose of the user of the mask. The holding loops 4 extend upwardly from that zone B of maximum width to the region of the eyes of the user of the mask. The inward edges of the through openings which are bordered by the holding loops 4 are of a rounded configuration in order to prevent the band portions which are passed through those openings from possibly being chafed through. This view again shows the latching device adapted for fixing the docking port in the carrier portion 7.

FIG. 6 shows the fixing plates 37 which are provided at the underside of the frame portion 3, from another perspective. The fixing plates 37 are of a thickness t as measured transversely to the joining direction in the range of from 0.8 to 3 mm. The fixing plates are of a tapered configuration in the joining direction. The fixing plates 37 and in particular also the internal peripheral region of the frame portion 3, which region bears against the arch body 2, can be provided with a profiling which still further assists with coupling of the arch body. Preferably, fine profile grooves extending in the peripheral direction of the frame portion 3 are provided on the frame portion 3 and on the portion of the arch body 2, which bears thereagainst.

The bayonet connecting structure 25 on the carrier portion 7 includes an end abutment 38 for defining the end position of the docking port 8 in the coupling position. In this embodiment the bayonet connecting structure 25 is designed in such a way that the maximum fixing force is achieved in the end position defined by the end abutment 38.

FIG. 7 shows the breathing mask arrangement according to the invention—with the exception of the forehead cushion elements 14 (FIG. 1) in the completely assembled condition, from the direction of the pivot axis X. As can be seen in that view the docking port 8 which in accordance with the invention can be releasably inserted into the carrier portion 7 forms a coupling element for coupling the elastomer arch body 2 to a rotatably supported hose connecting sleeve 9, by which the feed flow of respiratory gas is deflected through an angle α which in this embodiment is 32°.

The docking port 8 can be selected from a set which includes a plurality of docking ports 8 and forms an interface member by which the arch body 2 can be coupled to different hose systems. Compatibility with different respiratory gas conduit systems can also be ensured by way of the hose connecting sleeve 9 which is fitted on to the docking port 8. It is possible to provide a plurality of sealing lip means which are respectively adapted to given types of faces and to achieve a configuration which is appropriate to the requirements involved, for the breathing mask arrangement according to the invention, in that an elastomer element which takes particularly good account of the individual facial architecture of the user of the mask and which comprises the sealing lip means 1 and the arch body 2 is integrated into the mask arrangement according to the invention. It is also possible to provide a plurality of variants of the forehead support device, which however are compatible with the adjusting means 11, and to fit the mask arrangement according to the invention with a variant of the forehead supporting device 10 which takes particularly good account of the individual facial architecture. As an alternative to the forehead cushion elements shown in FIG. 1, the forehead supporting device 10 may also be fitted with other kinds of forehead cushion devices for cushioned contact against the forehead of the user of the mask. It is possible to integrate cushion devices of that kind, for example into an upper forehead band arrangement, and to fit the forehead supporting device on to that cushioned forehead band arrangement, for example by way of a hook-and-loop fastener structure.

The invention is not limited to the preceding embodiment. By way of example, it is also possible to fit into the frame portion 3 which is designed in accordance with the invention, an arch body 2 which is not made from an elastomer material.

The forehead support device shown in FIG. 8 has a holding device 41 for pivotably holding a contact element 42. The holding device 41 for that purpose includes a pivotable holder 43 which here has a plurality of fixing elements 44 which form part of a ball joint arrangement.

In the embodiment illustrated here, the contact element 42 is of a plate-like configuration and is formed from an elastomer material, here fully transparent silicone rubber. The contact element 42 is mounted tiltably about at least two axes in space by way of the fixing elements 44. In order to ensure as easy mobility as possible of the contact element 42, provided between the fixing elements 44 and a fixing shank portion (not visible) of the contact element 42 is a ring body which has a spherical external surface (details in relation thereto will be described more fully with reference to FIG. 9).

The holding device 41 further includes a coupling portion 45 for coupling the holding device 41 to a breathing mask 46.

In the embodiment illustrated here the coupling portion 55 is in the form of a ring-like element which can be fitted directly on to a connecting portion 47 of the breathing mask 46, the connecting portion 47 being of a correspondingly complementary configuration. In the embodiment illustrated here the holding device 41 is provided with a fixing portion 48 and can be connected by way thereof to a headband.

FIG. 9 shows a preferred embodiment of the contact element 42. The contact element 42 is formed from an elastomer material and has a contact surface 49 which is slightly concavely curved. The contact element 42 is provided with a plurality of fine through bores 50 through which pressure equalisation with the ambient atmosphere can be achieved in respect of the intermediate space possibly defined between the contact element 42 and the forehead of the patient. That advantageously prevents the contact element 42 from being sucked against the forehead region of the patient.

In the embodiment illustrated here the contact element 42 has a shank portion 51. Provided on the shank portion 51 is a ring element 52 which forms a spherical external surface. In conjunction with that ring element 52, this arrangement affords a comparatively easily movable ball joint device. As an alternative thereto it is also possible to forego the ring element and to provide the corresponding spherical portion directly on the shank portion 51 of the contact element 42.

The embodiment of the invention shown in FIG. 10 has two contact elements 42 which are connected together by way of an integral central bridge or strap 54. The central strap 54 is so designed that it still permits pivotal movement and tilting movement of the two contact elements 42 relative to each other over a sufficient angular range. The spacing of the centres of the two contact elements 42 from each other preferably approximately corresponds to the distance between the eyes of the user of the mask.

FIG. 11 shows a further embodiment of a contact element 42, in which case tiltability of the portion of the contact element, which forms the contact surface, is achieved by way of an elastomer structure 55 which here is formed integrally with the contact element 52. In the embodiment illustrated here the elastomer structure includes a substantially spherical internal space which can be fitted on to a spherical trunnion portion, with temporary elastic expansion. In the embodiment illustrated here the contact element also has a concavely curved base body which is flattened when the contact element is appropriately fitted in position.

The curvature of the base body of the contact element is preferably so selected that a defined distribution in terms of contact pressure is afforded when it is applied to a flat surface. That distribution in respect of contact pressure is shown by way of example in FIG. 12. The lower curved line a1 in this case symbolises the contact surface of the contact element in its initial position. The line a2 which is shown here as being straight symbolises the contact surface of the contact element 42, when appropriately deformed in the application position. The distribution in terms of surface pressure, which is indicated here in simplified form by an assembly of arrows 56, occurs in the context of deformation of the contact surface of the contact element. The distribution in terms of surface pressure is selected here in such a way that, starting from the centre Z towards the edge region, there is initially a substantially uniform distribution in terms of surface pressure, with the surface pressure gradually decreasing in the region of r/5 towards the edge R.

The invention is not limited to the embodiments described hereinbefore. For example, it is also possible, in a departure from the plate-shaped configuration selected here, for the forehead contact elements to be of a rectangular or polygonal configuration.

The invention claimed is:

1. A breathing mask arrangement for delivering breathable gas to a patient, comprising:
   a frame having an open construction that provides an annular mask retaining portion and a conduit carrier portion;
   a nasal mask having a body portion removably attachable within the mask retaining portion of the frame and a sealing portion structured to engage a patient's face generally along nasal bridge, cheek, and lip regions of the patient's face; and
   a conduit member releasably coupled to the conduit carrier portion of the frame and in fluid communication with the nasal mask to deliver breathable gas into a nasal breathing space of the nasal mask.

2. The breathing mask arrangement according to claim 1, further comprising a hose connector coupled to the conduit member, the hose connector structured to be connected to a gas delivery tube.

3. The breathing mask arrangement according to claim 2, wherein the conduit member includes an annular flange baying a plurality of tongue elements that are elastically deformable towards an axis of the conduit member, each of the tongue elements having a retaining ridge structured to engage the hose connector so as to rotatably couple the conduit member to the hose connector.

4. The breathing mask arrangement according to claim 1, wherein the body portion of the nasal mask includes a first side including said sealing portion and a second side defining a mask interior breathing chamber, the first and second sides being provided on opposite sides of the frame.

5. The breathing mask arrangement according to claim 1, wherein the body portion and the sealing portion are integrally formed in one piece.

6. The breathing mask arrangement according to claim 1, further comprising a forehead support supporting elastomeric forehead cushion elements that are structured to engage a patient's forehead, the forehead support being moveably coupled to the frame to allow movement of the forehead support relative to the frame along an arcuate path to thereby adjust the position of the forehead cushion elements relative to the patient.

7. The breathing mask arrangement according to claim 6, wherein the forehead support includes a pair of holding clips structured to be removably connectable to an upper band arrangement of a headband and the frame includes a pair of holding clips structured to be removably connectable to a lower band arrangement of the headband for maintaining the mask arrangement in a desired position on the patient face.

8. The breathing mask arrangement according to claim 1, wherein the mask retaining portion and the conduit cater portion are integrally formed in one piece.

9. The breathing mask arrangement according to claim 1, wherein the conduit carrier portion has an insert opening and the a conduit member can be releasably inserted into the insert opening.

10. The breathing mask arrangement according to claim 1, wherein the conduit member is releasably coupled to the conduit cater portion by a bayonet or rotary latching device.

11. The breathing mask arrangement according to claim 1, wherein the conduit carrier portion is oriented substantially transversely with respect to the mask retaining portion.

12. The breathing mask arrangement according to claim 4, wherein the first side is provided on one side of the mask retaining portion and the second side is provided on the opposite side of the mask retaining portion.

13. The breathing mask arrangement according to claim 1, wherein the annular mask retaining portion includes a ring-shaped configuration that defines an inwardly facing annular retaining surface adapted to engage an outwardly facing side wall of the body portion.

14. The breathing mask arrangement according to claim 1, wherein the annular mask retaining portion encloses or wraps around the body portion.

15. The breathing mask arrangement according to claim 1, wherein each end of the mask retaining portion is substantially open ended.

16. The breathing mask arrangement according to claim 1, wherein the body portion defines a mask interior breathing chamber.

17. The breathing mask arrangement according to claim 1, wherein the mask retaining portion includes fixing plates adapted to engage the body portion.

18. The breathing mask arrangement according to claim 1, wherein the mask retaining portion includes a recessed region adapted to receive a protruding nose of the body portion.

19. The breathing mask arrangement according to claim 1, wherein the nasal mask has a substantially saddle-shaped profile.

* * * * *

UNITED STATES PATENT AND TRADEMARK OFFICE
CERTIFICATE OF CORRECTION

PATENT NO. : 7,654,263 B2  Page 1 of 1
APPLICATION NO. : 11/128399
DATED : February 2, 2010
INVENTOR(S) : Lang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 903 days.

Signed and Sealed this

Twenty-eighth Day of December, 2010

David J. Kappos
*Director of the United States Patent and Trademark Office*